(12) United States Patent
Hornbach et al.

(10) Patent No.: US 10,943,678 B2
(45) Date of Patent: **\*Mar. 9, 2021**

(54) SEQUENTIAL COMPRESSION THERAPY COMPLIANCE MONITORING SYSTEMS AND METHODS

(71) Applicant: Hill-Rom Services, Inc., Batesville, IN (US)

(72) Inventors: David W. Hornbach, Brookville, IN (US); David L. Ribble, Indianapolis, IN (US); Christopher R. O'Keefe, Batesville, IN (US); Timothy J. Receveur, Guilford, IN (US); Thomas K. Skripps, Acton, MA (US)

(73) Assignee: Hill-Rom Services, Inc., Batesville, IN (US)

( * ) Notice: Subject to any disclaimer, the term of this patent is extended or adjusted under 35 U.S.C. 154(b) by 896 days.

This patent is subject to a terminal disclaimer.

(21) Appl. No.: 15/659,906

(22) Filed: Jul. 26, 2017

(65) Prior Publication Data

US 2017/0333279 A1 Nov. 23, 2017

Related U.S. Application Data

(63) Continuation of application No. 14/041,128, filed on Sep. 30, 2013, now Pat. No. 9,737,454, which is a
(Continued)

(51) Int. Cl.
*G16H 10/60* (2018.01)
*A61H 9/00* (2006.01)
(Continued)

(52) U.S. Cl.
CPC .......... *G16H 10/60* (2018.01); *A61B 5/0295* (2013.01); *A61B 5/02141* (2013.01);
(Continued)

(58) Field of Classification Search
CPC ........ A61H 9/00; A61H 9/005; A61H 9/0078; A61H 9/0092; A61H 2201/0184;
(Continued)

(56) References Cited

U.S. PATENT DOCUMENTS

| 891,181 A | 6/1908 | Mitchell |
|---|---|---|
| RE14,681 E | 7/1919 | Faries |

(Continued)

FOREIGN PATENT DOCUMENTS

| EP | 0 861 651 A1 | 9/1998 |
|---|---|---|
| EP | 0 992 230 A2 | 4/2000 |

(Continued)

OTHER PUBLICATIONS

Extended European Search Report for European Patent Application No. 17209100.1 dated Jun. 12, 2018; 11 pages.
(Continued)

*Primary Examiner* — Timothy A Stanis
(74) *Attorney, Agent, or Firm* — Barnes & Thornburg LLP (57) ABSTRACT

A system includes a sequential compression device (SCD) used by a patient as part of a sequential compression therapy (SCT) protocol. The system also includes a computer device that determines whether the SCD is in use in substantially real time in compliance with the protocol. The computer device initiates a notification to a caregiver if noncompliance with the SCT protocol is detected.

20 Claims, 6 Drawing Sheets

Related U.S. Application Data continuation-in-part of application No. 13/410,502, filed on Mar. 2, 2012, now abandoned.

(51) Int. Cl.

| | | |
|---|---|---|
| *A61H 7/00* | (2006.01) | |
| *A61B 5/00* | (2006.01) | |
| *A61B 5/021* | (2006.01) | |
| *A61B 5/0295* | (2006.01) | |
| *A61B 5/11* | (2006.01) | |
| *G16H 20/30* | (2018.01) | |
| *A61N 1/04* | (2006.01) | |
| *A61B 5/02* | (2006.01) | |

(52) U.S. Cl.
CPC .......... *A61B 5/1115* (2013.01); *A61B 5/4833* (2013.01); *A61B 5/7275* (2013.01); *A61H 7/00* (2013.01); *G16H 20/30* (2018.01); *A61B 5/02007* (2013.01); *A61B 9/0078* (2013.01); *A61H 2201/0184* (2013.01); *A61H 2201/10* (2013.01); *A61H 2201/501* (2013.01); *A61H 2201/5002* (2013.01); *A61H 2201/5012* (2013.01); *A61H 2201/5071* (2013.01); *A61H 2209/00* (2013.01); *A61H 2230/06* (2013.01); *A61H 2230/10* (2013.01); *A61H 2230/30* (2013.01); *A61N 1/0452* (2013.01); *A61N 1/0456* (2013.01)

(58) Field of Classification Search
CPC ........ A61H 2201/10; A61H 2201/5002; A61H 2201/501; A61H 2201/5012; A61H 2201/5071; A61H 2209/00; A61H 2230/06; A61H 2230/10; A61H 2230/30; A61B 5/0295; A61B 5/1115; A61B 5/4833; A61B 5/7275; A61B 5/02007; A61N 1/0452; A61N 1/0456
See application file for complete search history.

(56) References Cited

U.S. PATENT DOCUMENTS

| | | |
|---|---|---|
| 1,608,239 A | 11/1926 | Rosett |
| 2,361,242 A | 10/1944 | Rosett |
| 2,531,074 A | 11/1950 | Miller |
| 2,533,504 A | 12/1950 | Poor |
| 2,699,165 A | 1/1955 | Ferrier |
| 2,781,041 A | 2/1957 | Weinberg |
| 2,823,668 A | 2/1958 | van Court et al. |
| 2,880,721 A | 4/1959 | Corcoran |
| 2,896,612 A | 7/1959 | Bates et al. |
| 2,943,859 A | 7/1960 | Koski et al. |
| 3,094,116 A | 6/1963 | Logan et al. |
| 3,094,118 A | 6/1963 | De Besme et al. |
| 3,177,866 A | 4/1965 | Wesslund |
| 3,186,405 A | 6/1965 | Bailey et al. |
| 3,454,010 A | 7/1969 | Lilligren et al. |
| 3,548,809 A | 12/1970 | Conti |
| 3,811,431 A | 5/1974 | Apstein |
| 3,831,766 A | 8/1974 | Newman et al. |
| 3,865,102 A | 2/1975 | Birtwell et al. |
| 3,866,604 A | 2/1975 | Curless et al. |
| 3,868,952 A | 3/1975 | Hatton |
| 3,880,149 A | 4/1975 | Kawaguchi |
| 3,889,494 A | 6/1975 | Patience et al. |
| 3,892,229 A | 7/1975 | Taylor et al. |
| 3,896,794 A | 7/1975 | McGrath |
| 3,901,225 A | 8/1975 | Sconce |
| 3,982,531 A | 9/1976 | Shaffer |
| 4,013,069 A | 3/1977 | Hasty |
| 4,021,860 A | 5/1977 | Swallow et al. |
| 4,027,667 A | 6/1977 | Swallow et al. |
| 4,029,087 A | 6/1977 | Dye et al. |
| 4,030,488 A | 6/1977 | Hasty |
| 4,054,952 A | 10/1977 | Swallow |
| 4,069,515 A | 1/1978 | Swallow et al. |
| 4,089,068 A | 5/1978 | Swallow |
| 4,091,804 A | 5/1978 | Hasty |
| 4,156,425 A | 5/1979 | Arkans |
| 4,157,713 A | 6/1979 | Clarey |
| 4,180,869 A | 1/1980 | Pedergrass et al. |
| 4,198,961 A | 4/1980 | Arkans |
| 4,202,325 A | 5/1980 | Villari et al. |
| 4,207,875 A | 6/1980 | Arkans |
| 4,207,876 A | 6/1980 | Annis |
| 4,253,449 A | 3/1981 | Arkans et al. |
| 4,280,485 A | 7/1981 | Arkans |
| 4,311,135 A | 1/1982 | Brueckner et al. |
| 4,320,746 A | 3/1982 | Arkans et al. |
| 4,321,929 A | 3/1982 | Lemelson et al. |
| 4,331,133 A | 5/1982 | Arkans |
| 4,335,726 A | 6/1982 | Kolstedt |
| 4,369,588 A | 1/1983 | Berguer |
| 4,370,975 A | 2/1983 | Wright |
| 4,372,297 A | 2/1983 | Perlin |
| 4,374,518 A | 2/1983 | Villanueva |
| 4,375,217 A | 3/1983 | Arkans |
| 4,388,923 A | 6/1983 | Heimreid |
| 4,396,010 A | 8/1983 | Arkans |
| 4,402,312 A | 9/1983 | Villari et al. |
| 4,418,690 A | 12/1983 | Mummert |
| 4,424,596 A | 1/1984 | Jackson |
| 4,453,538 A | 6/1984 | Whitney |
| 4,481,937 A | 11/1984 | Arkans |
| 4,492,234 A | 1/1985 | Arkans |
| 4,502,301 A | 3/1985 | Swallow et al. |
| 4,513,740 A | 4/1985 | Westlake |
| 4,527,402 A | 7/1985 | Swallow et al. |
| 4,573,453 A | 3/1986 | Tissot |
| 4,577,626 A | 3/1986 | Marukawa et al. |
| 4,597,384 A | 7/1986 | Whitney |
| 4,614,179 A | 9/1986 | Gardner et al. |
| 4,614,180 A | 9/1986 | Gardner et al. |
| 4,624,244 A | 11/1986 | Taheri |
| 4,628,911 A | 12/1986 | Bornstein |
| 4,648,392 A | 3/1987 | Cartier et al. |
| 4,657,003 A | 4/1987 | Wirtz |
| 4,682,588 A | 7/1987 | Curlee |
| 4,696,289 A | 9/1987 | Gardner et al. |
| 4,702,232 A | 10/1987 | Gardner et al. |
| 4,721,101 A | 1/1988 | Gardner et al. |
| 4,722,332 A | 2/1988 | Saggers |
| 4,730,610 A | 3/1988 | Graebe |
| 4,744,391 A | 5/1988 | Lardner |
| 4,745,917 A | 5/1988 | Hasty et al. |
| 4,753,226 A | 6/1988 | Zheng et al. |
| 4,773,397 A | 9/1988 | Wright et al. |
| 4,793,328 A | 12/1988 | Kolstedt et al. |
| 4,804,208 A | 2/1989 | Dye |
| 4,805,601 A | 2/1989 | Eischen, Sr. |
| 4,809,684 A | 3/1989 | Gardner et al. |
| 4,827,912 A | 5/1989 | Carrington et al. |
| 4,832,010 A | 5/1989 | Lerman |
| RE32,939 E | 6/1989 | Gardner et al. |
| RE32,940 E | 6/1989 | Gardner et al. |
| 4,841,956 A | 6/1989 | Gardner et al. |
| 4,846,160 A | 7/1989 | Gardner et al. |
| 4,858,596 A | 8/1989 | Kolstedt et al. |
| 4,865,020 A | 9/1989 | Bullard |
| RE33,090 E | 10/1989 | Berguer |
| 4,922,893 A | 5/1990 | Wright et al. |
| 4,928,674 A | 5/1990 | Halperin et al. |
| 4,938,208 A | 7/1990 | Dye |
| 4,941,458 A | 7/1990 | Taheri |
| 4,945,905 A | 8/1990 | Dye et al. |
| 4,947,834 A | 8/1990 | Kartheus et al. |
| 4,966,396 A | 10/1990 | Dye |
| 4,971,044 A | 11/1990 | Dye |
| 4,989,589 A | 2/1991 | Pekanmaki et al. |
| 5,000,164 A | 3/1991 | Cooper |
| 5,005,567 A | 4/1991 | Gilman et al. |
| 5,007,411 A | 4/1991 | Dye |

(56) References Cited

U.S. PATENT DOCUMENTS

| | | |
|---|---|---|
| 5,014,681 A | 5/1991 | Heeman et al. |
| 5,022,387 A | 6/1991 | Hasty |
| 5,025,781 A | 6/1991 | Ferrari |
| 5,027,797 A | 7/1991 | Bullard |
| 5,031,604 A | 7/1991 | Dye |
| 5,074,285 A | 12/1991 | Wright |
| 5,080,089 A | 1/1992 | Mason et al. |
| 5,109,832 A | 5/1992 | Proctor et al. |
| 5,117,812 A | 6/1992 | McWhorter |
| 5,125,400 A | 6/1992 | Johnson, Jr. |
| 5,127,808 A | 7/1992 | Nichols et al. |
| 5,133,199 A | 7/1992 | Parikh et al. |
| 5,135,473 A | 8/1992 | Epler et al. |
| 5,139,479 A | 8/1992 | Peters |
| 5,176,624 A | 1/1993 | Kuehnreich |
| 5,179,941 A | 1/1993 | Siemssen et al. |
| 5,186,163 A | 2/1993 | Dye |
| 5,211,162 A | 5/1993 | Gillen, Jr. et al. |
| 5,218,954 A | 6/1993 | van Bemmelen |
| 5,226,898 A | 7/1993 | Gross |
| 5,263,473 A | 11/1993 | McWhorter |
| 5,288,286 A | 2/1994 | Davis |
| 5,307,791 A | 5/1994 | Senoue et al. |
| RE34,661 E | 7/1994 | Grim |
| 5,328,445 A | 7/1994 | Spahn et al. |
| 5,342,285 A | 8/1994 | Dye |
| 5,354,260 A | 10/1994 | Cook |
| 5,368,034 A | 11/1994 | Isner |
| 5,368,547 A | 11/1994 | Polando |
| 5,383,894 A | 1/1995 | Dye |
| 5,389,065 A | 2/1995 | Johnson, Jr. |
| 5,396,896 A | 3/1995 | Tumey et al. |
| D357,736 S | 4/1995 | Dye |
| D358,216 S | 5/1995 | Dye |
| 5,413,142 A | 5/1995 | Johnson et al. |
| 5,435,009 A | 7/1995 | Schild et al. |
| 5,437,610 A | 8/1995 | Cariapa et al. |
| 5,441,533 A | 8/1995 | Johnson et al. |
| 5,443,440 A | 8/1995 | Tumey et al. |
| 5,449,379 A | 9/1995 | Hadtke |
| D363,988 S | 11/1995 | Dye |
| D364,459 S | 11/1995 | Dye |
| D364,460 S | 11/1995 | Dye |
| D364,680 S | 11/1995 | Dye |
| 5,464,385 A | 11/1995 | Grim |
| 5,466,250 A | 11/1995 | Johnson, Jr. et al. |
| 5,478,119 A | 12/1995 | Dye |
| D367,115 S | 2/1996 | Barber et al. |
| 5,490,820 A | 2/1996 | Schock et al. |
| 5,496,262 A | 3/1996 | Johnson, Jr. et al. |
| D369,664 S | 5/1996 | Dye |
| D373,192 S | 8/1996 | Murphy et al. |
| 5,558,627 A | 9/1996 | Singer et al. |
| D374,931 S | 10/1996 | Cesaroni et al. |
| 5,562,091 A | 10/1996 | Foster et al. |
| D376,013 S | 11/1996 | Sandman et al. |
| 5,571,075 A | 11/1996 | Bullard |
| 5,575,762 A | 11/1996 | Peeler et al. |
| 5,584,798 A | 12/1996 | Fox |
| 5,588,954 A | 12/1996 | Ribando et al. |
| 5,588,955 A | 12/1996 | Johnson, Jr. et al. |
| 5,591,200 A | 1/1997 | Cone et al. |
| 5,596,770 A | 1/1997 | Kunesh |
| 5,611,096 A | 3/1997 | Bartlett et al. |
| 5,613,941 A | 3/1997 | Prengler |
| 5,626,556 A | 5/1997 | Tobler et al. |
| 5,630,238 A | 5/1997 | Weismiller et al. |
| 5,634,889 A | 6/1997 | Gardner et al. |
| 5,669,872 A | 9/1997 | Fox |
| 5,671,751 A | 9/1997 | Tumey et al. |
| 5,674,262 A | 10/1997 | Tumey |
| 5,676,639 A | 10/1997 | Schild |
| 5,688,225 A | 11/1997 | Walker |
| 5,711,760 A | 1/1998 | Ibrahim et al. |
| 5,713,954 A | 2/1998 | Rosenberg et al. |
| 5,715,548 A | 2/1998 | Weismiller et al. |
| 5,725,485 A | 3/1998 | Ribando et al. |
| 5,730,136 A | 3/1998 | Laufer et al. |
| 5,747,460 A | 5/1998 | Bylund et al. |
| 5,769,801 A | 6/1998 | Tumey et al. |
| 5,781,949 A | 7/1998 | Weismiller et al. |
| 5,783,563 A | 7/1998 | Antonsson et al. |
| 5,795,312 A | 8/1998 | Dye |
| 5,800,528 A | 9/1998 | Lederman et al. |
| 5,810,750 A | 9/1998 | Buser |
| 5,826,761 A | 10/1998 | Basaj |
| 5,833,711 A | 11/1998 | Schneider, Sr. |
| 5,840,049 A | 11/1998 | Tumey et al. |
| 5,843,007 A | 12/1998 | McEwen et al. |
| 5,865,722 A | 2/1999 | Heng |
| 5,868,690 A | 2/1999 | Eischen, Sr. |
| 5,876,359 A | 3/1999 | Bock et al. |
| 5,891,065 A | 4/1999 | Cariapa et al. |
| 5,916,183 A | 6/1999 | Reid |
| 5,917,414 A * | 6/1999 | Oppelt ................ A61B 5/0002 340/573.1 |
| 5,931,797 A | 8/1999 | Tumey et al. |
| 5,938,628 A | 8/1999 | Oguri et al. |
| 5,951,502 A | 9/1999 | Peeler et al. |
| 5,968,073 A | 10/1999 | Jacobs |
| 5,989,204 A | 11/1999 | Lina |
| 6,001,119 A | 12/1999 | Hampson et al. |
| 6,010,470 A | 1/2000 | Albery et al. |
| 6,022,327 A | 2/2000 | Chang |
| 6,036,662 A | 3/2000 | Van Brunt et al. |
| 6,047,424 A | 4/2000 | Osborne et al. |
| 6,080,120 A | 6/2000 | Sandman et al. |
| 6,119,291 A | 9/2000 | Osborne et al. |
| 6,129,688 A | 10/2000 | Arkans |
| 6,141,792 A | 10/2000 | Acker et al. |
| D434,150 S | 11/2000 | Tumey et al. |
| 6,149,674 A | 11/2000 | Borders |
| 6,171,270 B1 | 1/2001 | Gau |
| 6,193,679 B1 | 2/2001 | Quinn |
| D439,341 S | 3/2001 | Tumey et al. |
| 6,231,532 B1 | 5/2001 | Watson et al. |
| 6,249,198 B1 | 6/2001 | Clark et al. |
| 6,290,662 B1 | 9/2001 | Morris et al. |
| 6,296,617 B1 | 10/2001 | Peeler et al. |
| 6,315,745 B1 | 11/2001 | Kloecker |
| 6,319,215 B1 | 11/2001 | Manor et al. |
| 6,322,530 B1 | 11/2001 | Johnson, Jr. et al. |
| 6,355,008 B1 | 3/2002 | Nakao |
| 6,358,219 B1 | 3/2002 | Arkans |
| 6,361,512 B1 | 3/2002 | Mackay et al. |
| 6,368,357 B1 | 4/2002 | Schon et al. |
| 6,387,065 B1 | 5/2002 | Tumey |
| 6,436,064 B1 | 8/2002 | Kloecker |
| 6,440,093 B1 | 8/2002 | McEwen et al. |
| 6,447,467 B1 | 9/2002 | Barak |
| 6,450,981 B1 | 9/2002 | Shabty et al. |
| 6,463,934 B1 | 10/2002 | Johnson, Jr. et al. |
| 6,467,111 B1 | 10/2002 | Vrzalik et al. |
| 6,468,237 B1 | 10/2002 | Lina |
| 6,478,757 B1 | 11/2002 | Barak |
| 6,488,643 B1 | 12/2002 | Tumey et al. |
| 6,494,852 B1 | 12/2002 | Barak et al. |
| 6,524,239 B1 * | 2/2003 | Reed ................ A61B 5/0002 600/300 |
| 6,544,202 B2 | 4/2003 | McEwen et al. |
| 6,551,280 B1 | 4/2003 | Knighton et al. |
| 6,558,338 B1 | 5/2003 | Wasserman |
| 6,572,621 B1 | 6/2003 | Zheng et al. |
| 6,585,669 B2 | 7/2003 | Manor et al. |
| 6,589,194 B1 | 7/2003 | Calderon et al. |
| 6,589,267 B1 | 7/2003 | Hui |
| 6,592,534 B1 | 7/2003 | Rutt et al. |
| 6,611,979 B2 | 9/2003 | Welling et al. |
| 6,893,409 B1 | 5/2005 | Lina |
| 7,641,623 B2 | 1/2010 | Biondo et al. |
| 7,909,786 B2 | 3/2011 | Bonnefin et al. |
| 9,737,454 B2 | 8/2017 | Hornbach et al. |
| 2001/0000262 A1 | 4/2001 | McEwen et al. |
| 2001/0011393 A1 | 8/2001 | Brooke et al. |

(56) References Cited

U.S. PATENT DOCUMENTS

| | | | |
|---|---|---|---|
| 2002/0042583 | A1 | 4/2002 | Barak et al. |
| 2003/0139255 | A1 | 7/2003 | Lina |
| 2004/0127937 | A1 | 7/2004 | Newton |
| 2006/0058587 | A1 | 3/2006 | Heimbrock et al. |
| 2006/0258964 | A1 | 11/2006 | Biondo et al. |
| 2007/0049853 | A1 | 3/2007 | Adams |
| 2007/0143920 | A1 | 6/2007 | Frondorf et al. |
| 2007/0179521 | A1* | 8/2007 | Horvat ............... A61B 17/1355 606/201 |
| 2007/0180616 | A1 | 8/2007 | Newkirk et al. |
| 2008/0000477 | A1 | 1/2008 | Huster et al. |
| 2008/0169931 | A1 | 7/2008 | Gentry et al. |
| 2008/0235872 | A1 | 10/2008 | Newkirk et al. |
| 2009/0049610 | A1 | 2/2009 | Heimbrock et al. |
| 2009/0112630 | A1* | 4/2009 | Collins, Jr. ............. H04L 67/12 705/3 |
| 2009/0209830 | A1* | 8/2009 | Nagle ..................... A43B 7/147 600/301 |
| 2009/0234262 | A1 | 9/2009 | Reid, Jr. et al. |
| 2010/0076356 | A1 | 3/2010 | Biondo et al. |
| 2010/0125952 | A1 | 5/2010 | Frondorf et al. |
| 2011/0030141 | A1 | 2/2011 | Soderberg et al. |
| 2011/0082401 | A1 | 4/2011 | Iker et al. |
| 2011/0190675 | A1* | 8/2011 | Vess ..................... A61H 9/0092 601/152 |
| 2011/0210925 | A1 | 9/2011 | Pittenger et al. |
| 2011/0214234 | A1 | 9/2011 | Herman |
| 2012/0022414 | A1 | 1/2012 | Receveyr et al. |
| 2012/0029879 | A1 | 2/2012 | Sing et al. |
| 2012/0047652 | A1 | 3/2012 | Metz et al. |
| 2012/0047653 | A1 | 3/2012 | Metz et al. |
| 2012/0083712 | A1* | 4/2012 | Watson ............... A61H 9/0078 600/587 |
| 2012/0089419 | A1 | 4/2012 | Huster et al. |
| 2012/0110735 | A1 | 5/2012 | Andrienko et al. |
| 2012/0198627 | A1 | 8/2012 | Turner et al. |
| 2013/0048705 | A1 | 2/2013 | Tallent et al. |
| 2013/0145558 | A1 | 6/2013 | Bhai |
| 2013/0231596 | A1 | 9/2013 | Hornbach et al. |
| 2014/0031730 | A1 | 1/2014 | Hornbach et al. |

FOREIGN PATENT DOCUMENTS

| | | |
|---|---|---|
| EP | 2272479 A2 | 1/2011 |
| WO | WO 93/12708 | 7/1993 |
| WO | WO 99/11215 | 3/1999 |
| WO | 00/00155 A1 | 1/2000 |

OTHER PUBLICATIONS

Expressmedsupplies.com website, Jobst Ultrasheer 8-1 Revitaleg Portable Pneumatic Compression Leg Massager.

Notification of Transmittal of the International Search Report and the Written Opinion of the International Searching Authority, or the Declaration, dated May 17, 2013, International Application No. PCT/US2013/028629; International Filing Date—Mar. 1, 2013; Applicant—Hill-Rom Services, Inc., Authorized Officer—Blaine R. Copenheaver.

PCT International Search Report, dated May 17, 2013; International Application No. PCT/US2013/028629; International Filing Date—Mar. 1, 2013; Applicant—Hill-Rom Services, Inc., Date of Actual Completion of the International Search—Apr. 26, 2013, Authorized Officer—Blaine R. Copenheaver.

PCT Written Opinion of the International Searching Authority, dated May 17, 2013, , International Application No. PCT/US2013/028629; International Filing Date—Mar. 1, 2013; Applicant—Hill-Rom Services, Inc., Date of Completion of Opinion—Apr. 26, 2013, Authorized Officer—Blaine R. Copenheaver.

Search History, PCT Application No. PCT/US2013/028629, Date of Search—Apr. 26, 2013.

Advisory Action for U.S. Appl. No. 13/410,502 dated Sep. 9, 2016 (3 Pages).

Amendment for U.S. Appl. No. 13/410,502 dated Aug. 18, 2016 (12 Pages).

Final Office Action U.S. Appl. No. 13/410,502 dated Jun. 24, 2016 (35 Pages).

Amendment for U.S. Appl. No. 13/410,502 dated Apr. 21, 2016 (11 Pages).

Office Action for U.S. Appl. No. 13/410,502 dated Feb. 2, 2016 (36 Pages).

Amendment for U.S. Appl. No. 13/410,502 dated Jan. 5, 2016 (12 Pages).

Advisory Action for U.S. Appl. No. 13/410,502 dated Dec. 24, 2015 (3 Pages).

Amendment for U.S. Appl. No. 13/410,502 dated Dec. 8, 2015 (12 Pages).

Final Office Action for U.S. Appl. No. 13/410,502 dated Oct. 20, 2015 (20 pages).

Amendment for U.S. Appl. No. 13/410,502 dated Jun. 18, 2015 (8 Pages).

Office Action for U.S. Appl. No. 13/410,502 dated Mar. 31, 2015 (22 pages).

Response to Office Action dated Nov. 19, 2014 for U.S. Appl. No. 13/410,502 dated Mar. 12, 2015 (10 Pages).

Final Office Action for U.S. Appl. No. 13/410,502 dated Nov. 19, 2014 (17 Pages).

Response to Office Action dated Aug. 13, 2014 for U.S. Appl. No. 13/410,502 dated Oct. 27, 2014 (15 Pages).

Office Action for U.S. Appl. No. 13/410,502 dated Aug. 13, 2014 (25 pages).

Amendment for U.S. Appl. No. 13/410,502 dated Jan. 13, 2017 (12 Pages).

Office Action for U.S. Appl. No. 13/410,502 dated Oct. 20, 2016 (44 Pages).

* cited by examiner

SEQUENTIAL COMPRESSION THERAPY COMPLIANCE MONITORING SYSTEMS AND METHODS

CROSS-REFERENCE TO RELATED APPLICATIONS

This application is a continuation of U.S. application Ser. No. 14/041,128, filed Sep. 30, 2013, now U.S. Pat. No. 9,737,454, which is a continuation-in-part of U.S. application Ser. No. 13/410,502, filed Mar. 2, 2012, now abandoned, each of which is expressly incorporated herein by reference.

BACKGROUND

Sequential compression therapy (SCT) is often used for prevention of deep venous thrombosis (DVT). Traditionally monitoring compliance and the utilization of sequential compression therapy by a patient are accomplished by a caregiver. While various systems have been developed for monitoring sequential compression therapy, there is still room for improvement. Thus, a need persists for further contribution in this area of technology.

SUMMARY

The present disclosure includes one or more of the features recited in the appended claims and/or the following features which, alone or in any combination, may comprise patentable subject matter.

One embodiment of the system to track usage of a compression sleeve comprises a compression sleeve, a fluid supply operable to inflate the compression sleeve, a processor configured to control the operation of the fluid supply and a memory device configured to record duration of the inflation of the compression sleeve.

Another embodiment of the system to monitor compliance of a compression sleeve usage comprises a memory device configured to record usage of a compression sleeve, a processor configured to compare the usage with a predetermined threshold.

One embodiment of the method to monitor compliance of a compression sleeve usage comprises determining usage of a compression sleeve, comparing usage of a compression sleeve with a predetermined threshold and determining compliance by comparing usage of a compression sleeve with the predetermined threshold.

Another embodiment of a system to monitor compliance of a compression sleeve usage comprises a compression sleeve and a first processor mounted on the compression sleeve configured to determine duration of inflation of the compression sleeve and communicate with a second processor mounted on a person support apparatus.

According to some embodiments, a system may include a sequential compression device (SCD) that may be used by a patient as part of a sequential compression therapy (SCT) protocol and a computer device that may determine whether the SCD is in use in substantially real time in compliance with the protocol and that may initiate a notification to a caregiver if noncompliance with the SCT protocol is detected.

In some embodiments, the computer device may determine whether an excused non-use condition exists. The excused non-use condition may correspond to a caregiver being present in the room of the patient or may correspond to the patient being off a person support apparatus.

In some embodiments, the computer device may determine that the SCD should be in use currently. The determination that the SCD should be in use may be based on one or more of the following: a locating tag of the SCD being sensed in the patient's room, a locating tag attached to a compression sleeve of the SCD being sensed in the patient's room, a locating tag attached to an SCD pump of the SCD being sensed in the patient's room, and the patient being sensed to be in the patient's room. In this regard, the system may include a locating tag for tracking the location of the patient or a wristband for tracking the location of the patient.

The determination that the SCD should be in use may be based on an electronic order. The electronic order may be entered at the patient's bedside or may be stored in a patient's electronic medical record (EMR), for example. Alternatively or additionally, the determination that the SCD should be in use may be based on at least one risk factor of the patient. The risk factor may include the patient having poor circulation or that the patient is recovering from surgery.

In some embodiments, the SCD being in use may be determined based on detecting one or more of the following: an SCD pump is on, the SCD pump is blowing air, the SCD pump is moving fluid, a motor of the SCD pump is drawing current, a compression sleeve is connected to the SCD pump, the compression sleeve is inflated to a threshold pressure, the SCD pump experiences a threshold back pressure due to pressurization of the compression sleeve, or a threshold amount of force is sensed by a sensor indicative of force between the compression sleeve and the patient.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The accompanying drawings incorporated in and forming a part of the specification illustrate several aspects of the claimed subject matter and, together with the description, serve to explain the principles of the claimed subject matter. In the drawings:

DETAILED DESCRIPTION

The embodiments of the claimed subject matter and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be briefly mentioned or omitted so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments herein are merely illustrative and should not be construed as limiting the scope of the claimed subject matter, which is defined solely by the appended claims and applicable law. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein is used for the purpose of describing particular embodiments only, and is not intended to limit the scope of the claimed subject matter.

Unless defined otherwise, all technical and scientific terms used herein have the same meanings as commonly understood by one of ordinary skill in the art.

Figure 1:
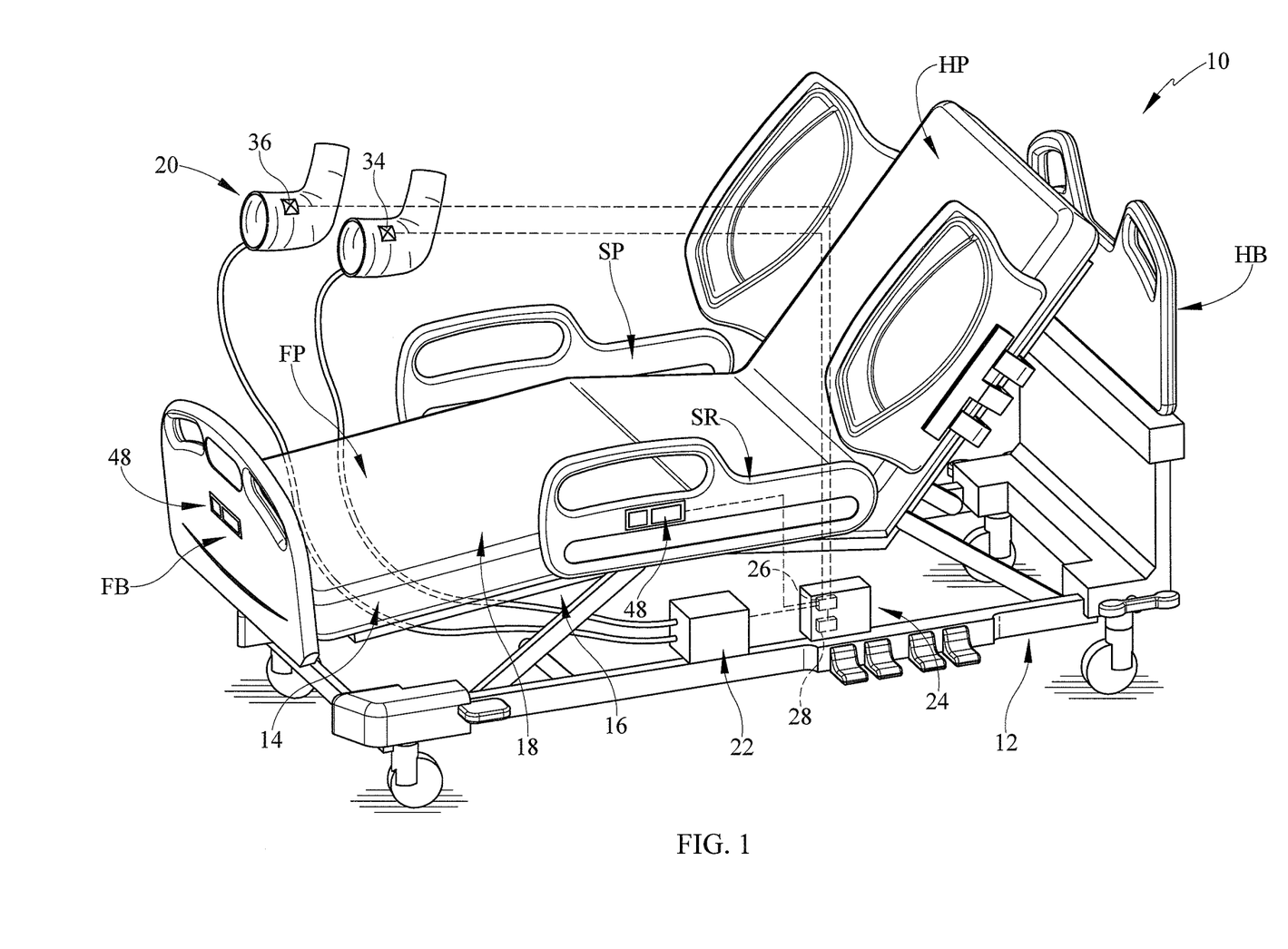
FIG. 1 is a perspective view of a system to track usage of a compression sleeve integrated with a hospital bed, constructed according to principles of one or more of the teachings herein.
Figure 2:
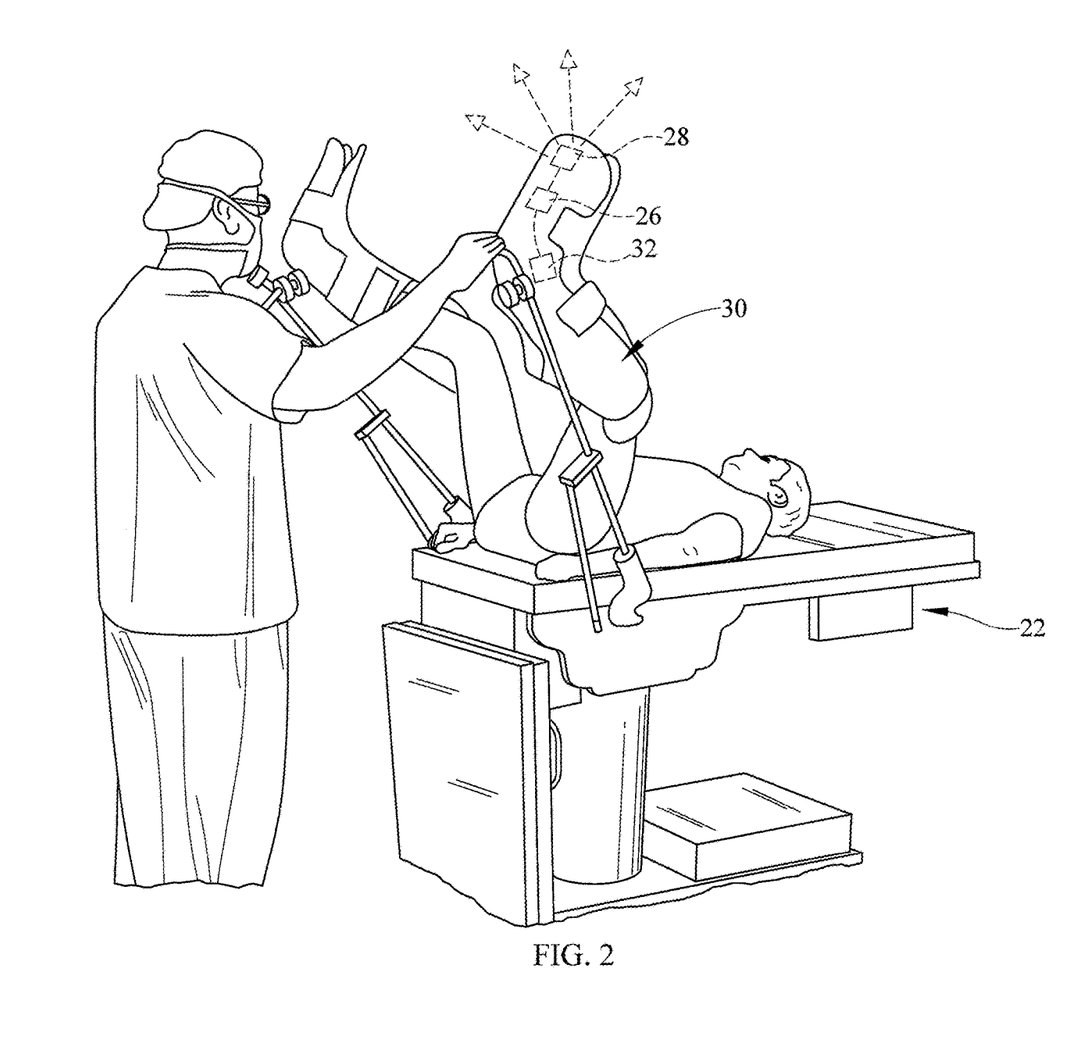
FIG. 2 is a perspective view of a system to track usage of a compression sleeve integrated with a fracture table, constructed according to principles of one or more of the teachings herein.

A person support apparatus 10 according to one illustrative embodiment of the current disclosure is shown in FIG. 1. In the illustrative embodiment as shown in FIG. 1, the person support apparatus 10 is a hospital bed. The person support apparatus 10 includes a lower frame or base 12, a plurality of supports 16 coupled with the lower frame 12, and an upper frame 14 supported by the plurality of supports above the lower frame 12. The upper frame 14 is configured to variably elevate with respect to the lower frame 12. A person support surface 18 is mounted on at least a portion of the person support apparatus 10. The person support surface 18 has a head support section HP, a seat support section SP and a foot support section FP as shown in FIG. 1. The person support apparatus 10 may be a stretcher or an operating table in another embodiment as shown in FIG. 2.

FIG. 1 illustrates a system to track usage of a compression sleeve comprising a fluid supply 22 mounted on the person support apparatus 10 and fluidly connected to the compression sleeve 20 using any one of a multitude of connection mechanisms, including quick disconnect type connectors. Compression sleeve 20 may be of any form, including but not limited to cuffs, boots and/or a wrap and may be customized to fit any body part. In one embodiment, the fluid supply 22 is removably mounted on the foot board FB, head board HB or the side rails SR. In another embodiment, the fluid supply 22 may be mounted on the compression sleeve 22. The fluid supply 22 may be used for other functions of the person support apparatus 10, including but not limited to inflation and/or deflation of a mattress.

In another embodiment, the system to track usage of a compression sleeve 20 comprises a dedicated fluid supply 22. The fluid supply 22 provides fluid to the compression sleeve 20 during inflation and vents the fluid from the compression sleeve 20 during deflation of the compression sleeve 20 in one embodiment. The fluid supply unit may be pneumatic or hydraulic in nature and may comprise a pump, blower, fan and/or a compressor. Therefore, the compression sleeve may be inflated with air, water, oil or any other fluid.

A controller 24 comprises a processor 26 in communication with the fluid supply 22 and provides a control signal to the fluid supply 22 to inflate or deflate the compression sleeve 20. The processor 26 also communicates with a pressure sensor 34 mounted on the compression sleeve 20 to allow measurement of the pressure inside the inflated compression sleeve 20 and/or the pressure applied on a patient's extremity to which the compression sleeve 20 is mounted. Alternatively, back pressure and/or electrical characteristics such as current and voltage changes of the prime mover of the fluid supply 22 may be used to determine the pressure in the compression sleeve in another embodiment.

An electrical stimulation device 36 is mounted in the compression sleeve 20 to provide appropriate therapy to the patient in some embodiments. The electrical stimulation device 36 may be of any type, including a Transcutaneous Nerve Stimulation (TENS) type for blocking pain and/or an Electro Muscle Stimulation (EMS) device for stimulating muscles. The electrical stimulation device 36 is in communication with and receives control signals from the processor 26 to initiate or terminate therapy. In one embodiment, the electrical stimulation device 36 receives power from the controller 24 while in another embodiment the electrical stimulation device 36 has a dedicated power source such as a battery pack.

The controller 24 is in communication with a Graphical User Interface (GUI) 48 to display alarms and other messages. The GUI 48 is integral to the person support apparatus 10 in one embodiment and is used to control other functions of the person support apparatus 10. The GUI 48 also allows for user inputs and commands to set thresholds for the amplitude, frequency and/or time duration of SCT and/or electrical stimulation therapy. These thresholds may be in the form of an upper bound (should not exceed), lower bound (should be greater than) and/or a range. The processor 26 uses these thresholds to determine compliance with prescribed therapy.

In one embodiment, the duration of cumulative therapy is tracked by the processor 26, by storing, in a memory device 28, data related to inflation and deflation of the compression sleeve 20 and/or operation of the electrical stimulation device. The memory device 28 may be of any type, including volatile and non-volatile types. If the cumulative duration of therapy does not meet the criteria established earlier, an alarm will be displayed on the GUI 48. Display of other performance characteristics of the therapy on the GUI 48 is well within the scope of this disclosure, including, but not limited to cumulative duration of therapy, duration of therapy of current session, average amplitude of therapy which in one embodiment may be the pressure and/or the electrical stimulation applied and frequency of therapy. The GUI 48 also allows a user to clear previously stored data in the memory device 28 and/or initiate therapy. In another embodiment, the system to track usage of a compression sleeve includes a dedicated GUI 48, which may be in the form of a pendant.

Figure 3:
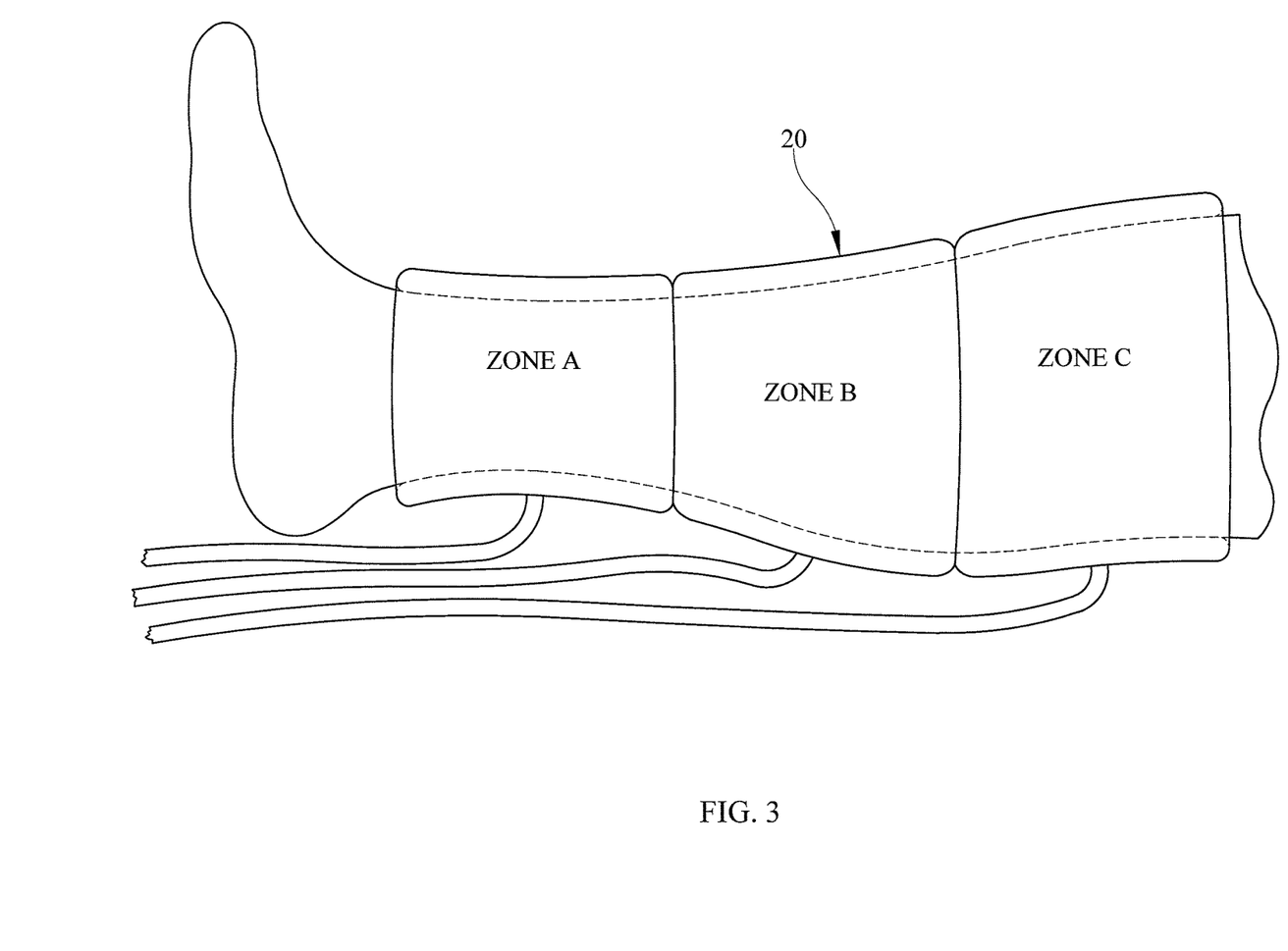
FIG. 3 is a side view of a compression sleeve mounted on a patient's leg, constructed according to principles of one or more of the teachings herein.

The illustrative embodiment of FIG. 2 shows a compression sleeve 20 mounted in a stirrup 30 used in conjunction with an operating table. In the embodiment shown in FIG. 2, the processor 26 and the memory device 28 are mounted on the compression sleeve 20. The compression sleeve 20 is configured to couple to a fluid supply 22 mounted on the operating table using any type of connection mechanism, including a quick disconnect mechanism. In another embodiment, the fluid supply 22 may be mounted on the stirrup 30 or the compression sleeve 20. The processor 26 and/or the memory device 28 wirelessly communicate with a communication network 40 (FIG. 3). The communication network 40 is in turn connected to a GUI 48, not shown in FIG. 2 and the GUI 48 allows for inputting commands, display of messages and/or for communicating alarms received from the processor 26 and/or the memory device 28.

The illustrative embodiment as shown in FIG. 2 also has a physiological sensor 32 mounted on the compression sleeve 22 in communication with the processor 26. It is well within the scope of the disclosure to include more than one physiological sensor 32 in the system. Physiological sensor 32 may be of any type and communicates with the processor 26 by way of an electrical signal indicative of at least one physiological parameter, including but not limited to temperature, blood pressure, heart rate and electrical activity. Processor 26 monitors the signals from the physiological sensor 32 and is configured to communicate an alarm to the GUI 48 in response to any of the physiological parameters not complying with a predetermined rule or threshold.

The GUI 48 is also configured to display data obtained from physiological sensors 32 via processor 26. The illustrative embodiment as shown in FIG. 2 allows for the same compression sleeve to be used in post-operative care as was used during an operation. This transfer from an operating room to post-operative care often involves changing rooms and/or person support apparatus 10. Since the system as shown in FIG. 2 allows for mounting the processor 26 and memory device 28 on the compression sleeve 22, a continuous stream of data is available and a cumulative usage of the compression sleeve may be determined. The processor 26 and/or memory device 28 are configured to communicate with other controllers comprising processors and/or GUIs which in one embodiment may be remote. The processor 26 and/or the memory device 28 may communicate with a controller comprising a processor and/or GUI 48 integral to a patient support apparatus 10 via a wireless or wired connection based on the physical distance between the two devices. Thus, as the patient is moved from the operating room to a post-operative room, the processor 26 and/or the memory device 28 automatically connects with the controller of the person support apparatus 10 in the post-operative room. As described earlier, a fluid supply 22 mounted on the compression sleeve 20 allows for continued therapy during patient transfer.

The illustrative embodiment of FIG. 3 shows one embodiment of a compression sleeve 20 for use in the system to track usage of a compression sleeve. FIG. 3 shows the compression sleeve 20 used for sequential compression therapy of the patient's calf region. As shown in FIG. 3, the compression sleeve 20 has more than one zone in this embodiment, although a single pressurized zone is well within the scope of the current disclosure. The sleeve as shown in FIG. 3 has fluid supply lines connected to each zone, although a single supply line to all the zones may be used in another embodiment.

Figure 4:
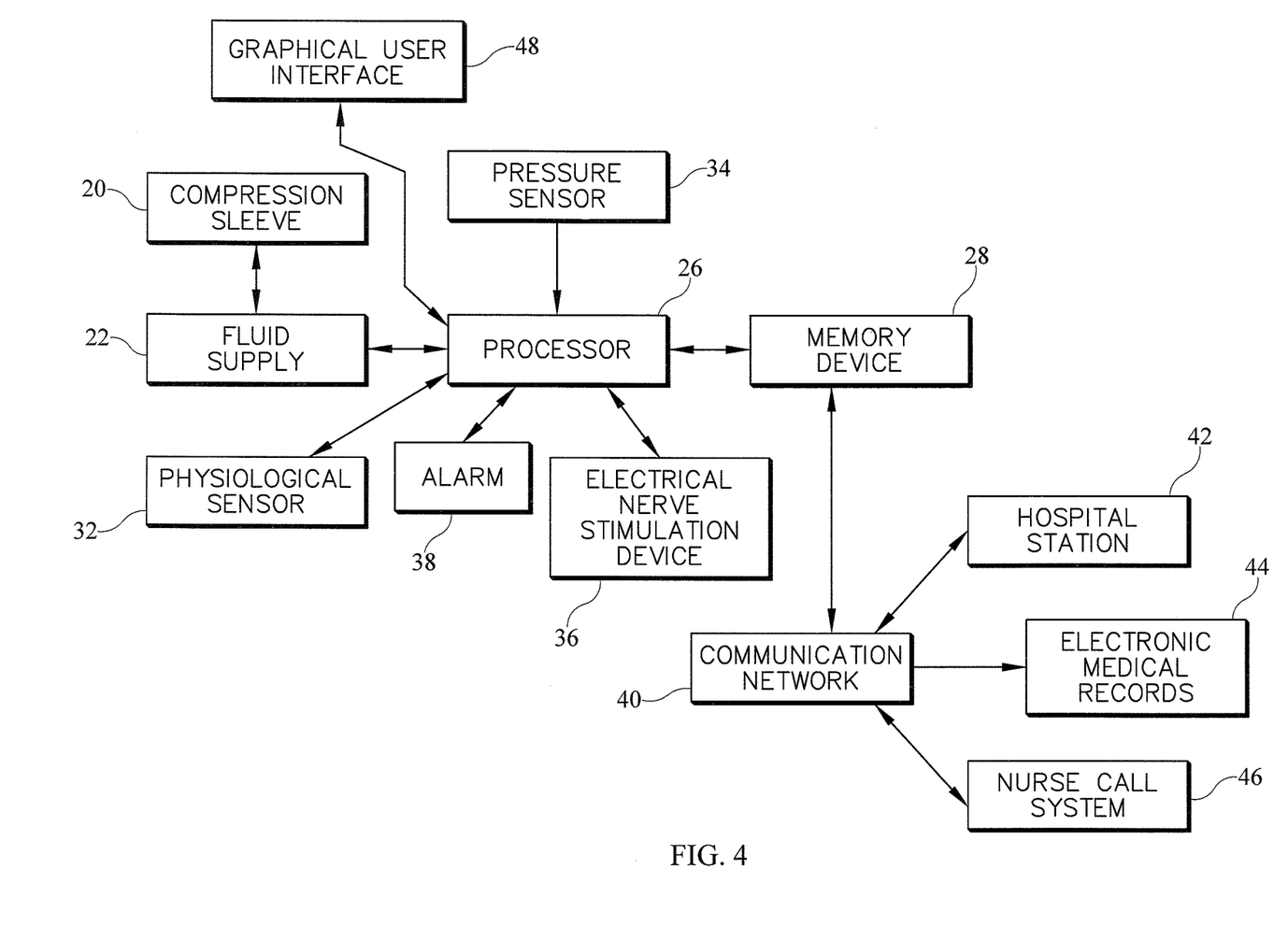
FIG. 4 is a block diagram of a system to monitor compliance of a compression sleeve, integrated with a hospital bed, constructed according to principles of one or more of the teachings herein.

FIG. 4 shows a block diagram of one embodiment of the system to track usage of a compression sleeve. The compression sleeve 20 is supplied fluid by a fluid supply 22, which in turn receives a control signal from the processor 26. At least one pressure sensor 34 mounted in the compression sleeve is in electrical communication with the processor 26. At least one electrical stimulation device 36 is also in communication with the processor 26. The processor 26 communicates with a memory device 28 and records parameters related to the sequential compression therapy, including, but not limited to any one or combination of the cumulative duration of therapy, duration of therapy for an individual session, amplitude and frequency of pressure applied. The processor 26 also conveys data corresponding to the signals received from at least one physiological sensor 32 and the electrical stimulation device 36 to the memory device 28. The processor 26 is also in communication with an alarm 38, which may be any combination of an audio, visual or tactile output. The processor 26 is configured to enable the alarm 38 based on the thresholds for sequential compression therapy, signals from the electrical stimulation device 36 and/or the physiological sensor 32. The processor 26 is in communication with a graphical user interface (GUI) 48 which allows for input of control parameters by a user and for display of system messages. Alarm 38 may be triggered and in another embodiment a timer may be activated for the alarm to trigger after a predetermined time period.

In the illustrative embodiment shown in FIG. 4, the memory device 28 is connected to a communication network 40. The communication network 40 may be of any type, including but not limited to Wide Area Network (WAN), Local Area Network (LAN), Virtual Private Network (VPN), telephone lines, optical communications, internet communications or telex. The communication network 40 is in communication with at least one Electronic Medical Record (EMR) 44 or another healthcare information database, a hospital communication station 42 and a nurse call system 46. The communication station 42 is a centralized location wherein one or more patients may be monitored by a caregiver. In one embodiment the communication station 42 may be stationary, while in another embodiment, it may be a mobile unit to accommodate prompt deployment.

Figure 5:
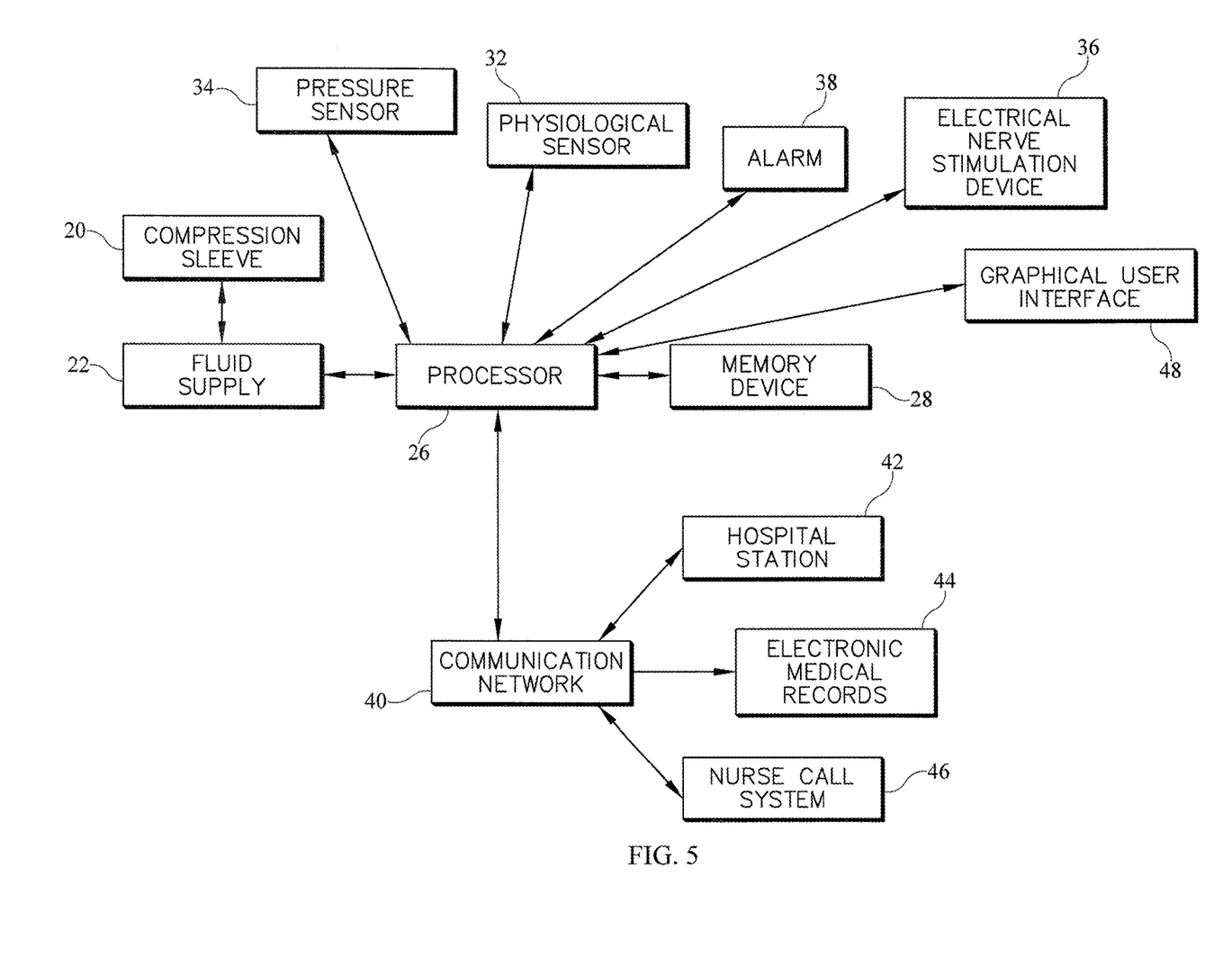
FIG. 5 is a block diagram of another system to monitor compliance of a compression sleeve, integrated with a hospital bed, constructed according to principles of one or more of the teachings herein.

In the illustrative embodiment shown in FIG. 5, the processor 26 is connected to a communication network 40. The communication network 40 may be of any type, including but not limited to Wide Area Network (WAN), Local Area Network (LAN), Virtual Private Network (VPN), telephone lines, optical communications, internet communications or telex. The communication network 40 is in communication with at least one Electronic Medical Record (EMR) 44 or another healthcare information database, a hospital communication station 42 and/or a nurse call system 46. The communication station 42 is a centralized location wherein one or more patients may be monitored by a caregiver. In one embodiment the communication station 42 may be stationary, while in another embodiment, it may be a mobile unit to accommodate prompt deployment.

According to this disclosure, a system and method is provided for determining noncompliance with a protocol relating to the use of a sequential compression device (SCD) as part of sequential compression therapy (SCT). The system determines that an SCD should be in use in substantially real time (aka that the device should be in use "at this moment")

and alerts one or more caregivers of the nonuse of the SCD so that the nonuse can be rectified. In order to determine compliance or non-compliance with the SCT protocol, the system first determines whether SCD use is required. This determination is made, in some embodiments, based on the detection of a physical trigger, such as a locating or tracking tag of an SCD being sensed in a particular location, such as a patient's room. In some embodiments, a tag attached to a compression sleeve and a tag attached to an SCD pump both need to be sensed in the same location in order for the system to determine that SCD use is required. Alternatively or additionally, a patient also needs to be sensed in the same location as the sleeve and/or pump. A patient wristband or location tag may be used to sense the location of the patient. Thus, in this latter embodiment, if a patient along with one or both of a compression sleeve and an SCD pump are determined to be in the same location (e.g., patient room), then the system makes the determination that the SCD device should be in use.

In other embodiments, an electronic order, such as one entered at the bedside or stored in a patient's electronic medical record (EMR) is considered by the system in making the determination that an SCD should be in use. In such embodiments, even if an SCD (e.g., pump and/or sleeve) is absent from a patient's location, if there is a physician's order for the patient to be undergoing SCT, then the system makes the determination that an SCD should be in use. Alternatively or additionally, based on other information in a patient's EMR or based on care setting, the system makes the determination that an SCD should be in use. For example, patients with poor circulation or other risk factors may be prescribed SCT after surgery for a certain number of hours in some healthcare facilities. Thus, based on information that a patient with such risk factors has just finished surgery, the system is able to make the determination that an SCD should be in use for that patient.

To summarize, there are a variety of ways contemplated by this disclosure to determine whether an SCD should be in use for a particular patient including the following: a tagged SCD pump has been placed in the patient's room; a tagged compression sleeve has been placed in the patient's room; a patient is designated as an at risk patient in the patient's EMR; the patient is designated as an at risk patient based on information transmitted from the patient's wristband; the patient is designated as an at risk patient based on a standard protocol; there is a physician's order for the patient to receive SCT; and/or the patient is in a particular location (e.g., all patients in post-op should be receiving SCT from an SCD).

Figure 6:
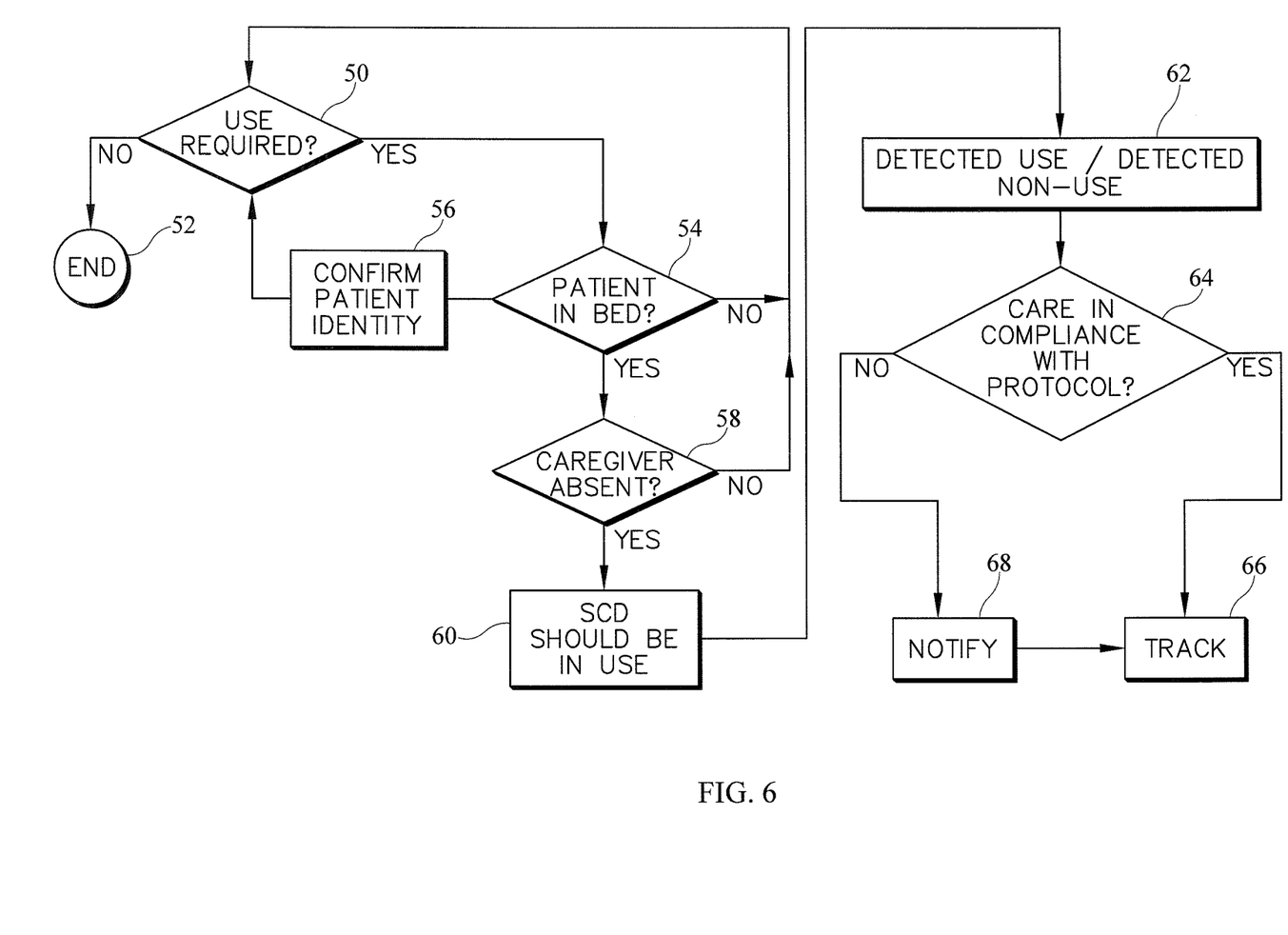
FIG. 6 is a flow chart showing steps of an algorithm to determine whether a patient is complying with a protocol requiring current use of a sequential compression device (SCD).

FIG. 6 is a flow chart of an algorithm that is illustrative of software that is run by a computer device, such as those included as part of hospital station 42, EMR 44, nurse call system 46 and/or processor 26 of person support apparatus 10. As indicated at block 50, the algorithm first determines whether use of an SCD is required for a particular patient. The various options for making this determination are discussed in the preceding paragraphs. If use of an SCD is not required for the patient, then the algorithm ends as indicated at block 42. If use of an SCD is required for the patient, the algorithm determines whether the patient is in bed as indicated at block 54. In connection with making such a determination, data from a bed exit system of the patient support apparatus 50 is used. In some embodiments, if a threshold amount of weight is detected on the bed, such as by use of one or more load cells of a weigh scale system as is well-known in the art, then it is assumed that the patient is in bed.

In some embodiments, the algorithm of FIG. 6 checks to confirm patient identity as indicated at block 56. Thus, in a first iteration of the algorithm in those instances when use of an SCD is required, the algorithm loops through blocks 50, 54, 56 to confirm patient identity. This, confirmation is made that the particular patient requiring SCT is actually the patient in bed, as opposed to a visitor or caregiver or some other patient sitting or lying on the bed rather than the patient in need of SCT. According to this disclosure, the patient's identity can be confirmed in a number of ways. For example, if the patient has a tag or wristband that transmits a patient ID, then a locating and tracking system confirms the patient's identity. Alternatively or additionally, a caregiver confirms the patient's identity and enters the information manually on the GUI 48 of person support apparatus 10. In some embodiments, bed 10 includes a biometric sensor that reads a patient's biometrics (e.g., fingerprint scanner, retinal scanner, camera and software for facial recognition, etc.) and confirms the patient's identity by comparison of the sensed information with that stored in a remote database, for example.

If at block 54, the patient is not in bed, then algorithm loops back to block 50 without checking the patient's identity. The patient being out of bed is considered to be one of the situations in which non-use of the SCD is excused according to some embodiments. For example, the patient may be going to the bathroom or may be scheduled for therapy or lab work in a different area of the healthcare facility. After the patient's identity is confirmed at block 56 and the patient is in bed as determined at block 54, then the second iteration through block 54 results in the algorithm advancing to block 58 and making a determination that no caregiver is present in the patient's room. If a caregiver is present in the patient's room, then this is also considered an excused non-use of the SCD by the patient, the assumption being that a caregiver may be attending to other medical needs of the patient or may be replacing a soiled compression sleeve or performing some other task. If at block 58 it is determined that caregivers are absent from the patient's room, then the SCD should be in use as indicated at block 60.

After it is determined that the SCD should be in use, the algorithm proceeds to make the determination regarding whether or not the SCD is actually in use currently by the patient as indicated at block 62. This determination is made based on data transmitted by compression sleeve 20 and/or fluid supply 22. For example, data indicating that the pump is active and/or that various zones of sleeve 20 are being pressurized is indicative that the SCD is in use currently. In some embodiments, a detected use involves detecting one or more of the following: the SCD pump is on, the SCD pump is blowing air (or moving other fluid), the motor of the SCD pump is running or drawing current, the compression sleeve is connected to the pump, the compression sleeve is inflated to a threshold pressure, the pump experiences a threshold back pressure due to pressurization of the compression sleeve, and/or a threshold amount of force is sensed by a sensor (e.g., piezoelectric sensor or force sensitive resistor (FSR)) positioned between the sleeve and the patient or otherwise positioned to sense pressure between the sleeve and the patient. On the other hand, if the one or more conditions just described are not detected, then this corresponds to a detected non-use. So, if no pump or sleeve is determined to be located in the room, if the pump is not operating, or if the sleeve is not being pressurized, then the algorithm determines at block 60 that there is a detected non-use condition.

After the use or non-use of the SCD is detected at block 62, the algorithm proceeds to block 64 and determines whether the use or non-use detected at block 62 is in compliance with the protocol for the associated patient. For example, even if the SCD is not in use, it could be that the duration of the SCT has expired or rest periods are permitted within the scope of the protocol. Thus, a detected non-use does not necessarily indicate a violation of the protocol. If at block 64 it is determined that the use or non-use of the SCD is in compliance with the protocol, then algorithm 66 proceeds to block 66 and tracks the use or non-use of the SCD. For example, the starting and ending times of the SCT are tracked in some embodiments. Alternatively or additionally, the frequency and/or pressure set points are tracked. Tracking refers to storing information in a database regarding the use and/or non-use of the SCD.

If at block 64 it is determined that the use or, more likely, the non-use of the SCD is not in compliance with the protocol, the algorithm proceeds to block 68 and notifies a caregiver of the noncompliance. After the notification, the algorithm proceeds to block 66 and data continues to be tracked even in the event of non-compliance. In the event of noncompliance with the SCT protocol, a number of solutions for achieving compliance may be undertaken according to this disclosure. For example, a caregiver is reminded of the protocol, such as via a message to a communication device carried by the caregiver, and guided to implement the SCT. A caregiver is notified that a patient has disabled the SCT and the caregiver can then work with the patient to address the issue and convince the patient of the benefits of compliance with the SCT protocol.

In some embodiments, a nurse manager is notified of the noncompliance and provides further training to an assigned caregiver regarding the value of the SCT and protocol compliance. Optionally, hospital administrators are able to track and reward continually increasing compliance with the SCT protocol. Hospital administrators may also use the gathered information of compliance and noncompliance with the SCT protocol to demonstrate a correlation between protocol compliance and improved patient outcomes. Furthermore, it is contemplated by this disclosure that the data regarding SCT protocol compliance is stored in other healthcare information systems such as the EMR 44.

In connection with the locating and tracking tags mentioned above, it will be appreciated that locating and tracking system are known in the art. See, for example, U.S. Pat. Nos. 8,421,606; 7,907,053; 7,734,476; 7,450,024; 7,248,933; 7,242,306; 6,972,683; and 6,825,763, each of which is hereby expressly incorporated by reference herein.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

The invention claimed is:

1. A person support apparatus for use with a compression sleeve, the person support apparatus comprising
   a frame,
   a fluid supply carried by the frame and operable to inflate the compression sleeve,
   a controller coupled to the frame and configured to control operation of the fluid supply, and
   at least one sensor coupled to the controller, the controller being configured to determine whether a patient is present on the patient support apparatus based on one or more signals from the at least one sensor, the controller being configured to determine whether the compression sleeve should be in use based on a protocol, wherein the controller is configured to initiate a notification to a caregiver if noncompliance with the protocol is detected, and wherein the controller determines compliance with the protocol only after the controller determines that the patient is present on the patient support apparatus based on the one or more signals from the at least one sensor.

2. The person support apparatus of claim 1, wherein the controller is configured to communicate data with a communication network.

3. The person support apparatus of claim 1, wherein the controller is configured to communicate with an electronic medical record system.

4. The person support apparatus of claim 1, wherein the controller is configured to communicate with a nurse call system.

5. The person support apparatus of claim 1, further comprising a pressure sensor configured to communicate pressure to the controller.

6. The person support apparatus of claim 5, wherein the pressure sensor is configured to measure pressure inside the compression sleeve.

7. The person support apparatus of claim 5, wherein the pressure sensor is configured to measure pressure that the compression sleeve applies to a person wearing the compression sleeve.

8. The person support apparatus of claim 1, wherein the controller is configured to compare data relating to usage of the compression sleeve with a predetermined threshold to determine compliance with the protocol.

9. The person support apparatus of claim 8, wherein the data relating to usage comprises one or more of frequency data, amplitude data, and duration of usage data.

10. The person support apparatus of claim 1, further comprising at least one physiological sensor configured to communicate at least one physiological signal to the controller.

11. The person support apparatus of claim 10, wherein the controller is configured to trigger an alarm if A) said at least one physiological signal is outside a predetermined range, or B) the duration of inflation of the compression sleeve is below a predetermined threshold, or C) the at least one physiological signal is outside the predetermined range, and the duration of inflation of the compression sleeve is below the predetermined threshold.

12. The person support apparatus of claim 1, wherein the controller is configured to record a frequency of compressive therapy provided by the compression sleeve.

13. The person support apparatus of claim 1, wherein the controller is configured to record an amplitude of compression applied by the compression sleeve.

14. The person support apparatus of claim 1, wherein the controller is configured to record a duration of application of compressive therapy by the compression sleeve.

15. The person support apparatus of claim 1, further comprising a display unit coupled to the frame, wherein the display unit is configured to display data relating to usage of the compression sleeve.

16. The person support apparatus of claim 1, wherein the controller is configured to determine whether the compression sleeve is in use according to the protocol in substantially real time if the patient is present on the patient support apparatus.

17. The person support apparatus of claim 1, wherein the controller is configured to determine whether an excused non-use condition exists such that the notification for non-compliance with the protocol is not initiated by the controller.

18. The person support apparatus of claim 17, wherein the excused non-use condition corresponds to a caregiver being present in a room with a patient.

19. The person support apparatus of claim 17, wherein the excused non-use condition corresponds to a patient being off of the person support apparatus.

20. The person support apparatus of claim 1, further comprising an electrical stimulation device coupled to the controller and configured to stimulate nerves or muscles of a patient.

* * * * *